(12) United States Patent
Parker

(10) Patent No.: US 7,462,674 B2
(45) Date of Patent: Dec. 9, 2008

(54) OXATHIAZAPHOSPHOLIDINE FREE RADICAL CONTROL AGENT

(75) Inventor: Dane Kenton Parker, Massillon, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 11/975,313

(22) Filed: Oct. 18, 2007

(65) Prior Publication Data

US 2008/0097057 A1   Apr. 24, 2008

Related U.S. Application Data

(62) Division of application No. 11/037,492, filed on Jan. 18, 2005, now Pat. No. 7,345,186.

(51) Int. Cl.
*C08F 2/00* (2006.01)
(52) U.S. Cl. .................. 526/193; 558/81; 514/102; 514/109; 514/99
(58) Field of Classification Search .................. 526/193; 558/81; 514/102, 109, 99
See application file for complete search history.

(56) References Cited

U.S. PATENT DOCUMENTS

| 6,153,705 | A | 11/2000 | Corpart et al. | 525/244 |
|---|---|---|---|---|
| 6,812,291 | B1 | 11/2004 | Corpart et al. | 525/244 |
| 2004/0073042 | A1 | 4/2004 | Charmot et al. | 546/335 |

FOREIGN PATENT DOCUMENTS

| WO | WO 98/01478 | 1/1998 |
|---|---|---|
| WO | WO 98/58974 | 12/1998 |
| WO | WO 99/31144 | 6/1999 |
| WO | WO 99/35177 | 7/1999 |

OTHER PUBLICATIONS

Bertrand et al., J. Org. Chem. 1995, 60, 3904-3906.*
Bonnet et al., *Macromol. Rapid. Commun.*, 2004, 25, 873-877.
Dubau-Assibat et al, *J. Org. Chem*, 1995, 60(12): CAS: 123:8809.

* cited by examiner

*Primary Examiner*—Robert D. Harlan
(74) *Attorney, Agent, or Firm*—Alvin T. Rockhill

(57) ABSTRACT

This invention discloses a process for producing a polymer by controlled polymerization which comprises polymerizing at least one monomer in the presence of a free radical control agent of the structural formula: $(Z)\text{-}(R^1)_n$, wherein n represents an integer from 1 to about 6; wherein Z represents an aromatic or aliphatic moiety containing from 1 to about 20 carbon atoms; wherein $R^1$ represents a moiety of the structural formula:

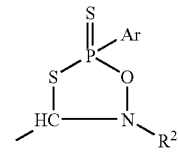

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

20 Claims, No Drawings

OXATHIAZAPHOSPHOLIDINE FREE RADICAL CONTROL AGENT

This is a divisional application of U.S. patent application Ser. No. 11/037,492, filed on Jan. 18, 2005, now U.S. Pat. No. 7,345,186.

FIELD OF THE INVENTION

The present invention relates to new compounds that are useful in assisting in the polymerization of monomers in a free radical polymerization that has living-type kinetics. Polymers made with the control agents and processes for polymerization are also included.

BACKGROUND OF THE INVENTION

The use and mechanism of control agents for free radical polymerization is now generally known (see U.S. Pat. No. 6,153,705, WO 98/01478, WO 99/35177, WO 99/31144, WO 98/58974, and United States Patent Application 20040073042). However, there remains a need for new agents that may lead to a commercially viable process. In particular, control agents that work to control the polymerization of vinyl monomers are of interest. Typical examples of vinyl monomers include styrene, (meth)acrylates, (meth)acrylamides, and the like. The control agents described in WO 98/01478, WO 99/35177, WO 99/31144, WO 98/58974, and United States Patent Application 20040073042 generally operate according to a reversible addition-fragmentation transfer mechanism, which confers a "living" character to the free radical polymerization of ethylenic monomers.

In general the commercial potential of controlled free radical polymerization (CFRP) is enormous. It has always been desirable to prepare well-defined homogeneous, block, graft, gradient, star, comb, end-functional and many other materials by free radical means under mild reaction conditions. This rapidly emerging ability via CFRP techniques is perhaps the most likely reason we are currently witnessing an explosion in academic and industrial interest with thousands of papers and hundreds of patents over the last five years. Recent estimates indicate that CFRP could easily affect a market of $20,000,000,000 per year across a very wide range of polymer applications.

United States Patent Application 20040073042 discloses control agents that have an O—N bond covalently bonded to a thiocarbonyl moiety. In some embodiments of United States Patent Application 20040073042 the control agents are of the general formula:

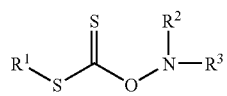

wherein $R^1$ is generally any group that is sufficiently labile to be expelled as its free radical form; $R^2$ and $R^3$ are each independently selected from the group consisting of hydrogen, hydrocarbyl, substituted hydrocarbyl, heteroatom-containing hydrocarbyl, and substituted heteroatom-containing hydrocarbyl, and combinations thereof, and optionally, $R^3$ combines with $R^2$ to form a ring structure, with said ring having from 3 to 50 non-hydrogen atoms.

In an alternative embodiment of United States Patent Application 20040073042 the control agent is a ring structure, which upon ring opening may form a multi-functional control agent. These cyclic control agents are of the structural formula:

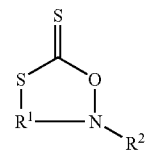

wherein $R^1$ is a bifunctional moiety that is sufficiently labile to be expelled as its free radical form; wherein $R^2$ and $R^3$ are each independently selected from the group consisting of hydrogen, hydrocarbyl, substituted hydrocarbyl, heteroatom-containing hydrocarbyl, and substituted heteroatom-containing hydrocarbyl, and combinations thereof, and wherein $R^3$ can optionally combine with $R^2$ to form a ring structure, with said ring having from 3 to 50 non-hydrogen atoms.

SUMMARY OF THE INVENTION

The present invention relates to compounds that are particularly useful as free radical control agents. These compounds are of the structural formula: $(Z)-(R^1)_n$, wherein n represents an integer from 1 to about 6; wherein Z represents an aromatic or aliphatic moiety containing from 1 to about 20 carbon atoms; wherein $R^1$ represents a moiety of the structural formula:

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms The present invention also discloses a process for producing a polymer by controlled polymerization which comprises polymerizing at least one monomer in the presence of a free radical control agent of the structural formula: $(Z)-(R^1)_n$, wherein n represents an integer from 1 to about 6; wherein Z represents an aromatic or aliphatic moiety containing from 1 to about 20 carbon atoms; wherein $R^1$ represents a moiety of the structural formula:

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

The present invention further reveals an emulsion polymerization process that comprises: (1) preparing a aqueous polymerization medium which is comprised of (a) at least one monomer, (b) a polymerization control agent, and an emulsifier, wherein the emulsifier is prepared in-situ within the aqueous polymerization medium; and (2) initiating polymerization of said monomer within the aqueous polymerization medium, wherein the polymerization control agent is of the structural formula: $(Z)\text{-}(R^1)_n$, wherein n represents an integer from 1 to about 6; wherein Z represents an aromatic or aliphatic moiety containing from 1 to about 20 carbon atoms; wherein $R^1$ represents a moiety of the structural formula:

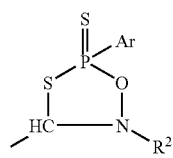

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

The present invention further reveals an emulsion polymerization process that comprises: (1) preparing a monomer solution which is comprised of (a) at least one monomer, (b) a conjugate acid of a surfactant with a $pK_a$ of less than about 14, and (c) a controlled free radical polymerization agent, wherein the polymerization control agent is of the structural formula: $(Z)\text{-}(R^1)_n$, wherein n represents an integer from 1 to about 6; wherein Z represents an aromatic or aliphatic moiety containing from 1 to about 20 carbon atoms; wherein $R^1$ represents a moiety of the structural formula:

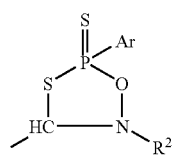

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms; (2) preparing an aqueous medium which is comprised of (a) water, and (b) a conjugate base of a weak acid wherein the $pK_b$ of the base is less than about 14; and (3) mixing the monomer solution with the aqueous medium under conditions that result in the in-situ formation of an emulsifier, and (4) initiating free radical polymerization. In such emulsion polymerizations the latent surfactant can be a conjugate acid of an anionic surfactant, wherein the $pK_a$ of the acid is less than about 14 or the latent surfactant can be a conjugate base of an anionic surfactant, wherein the $pK_b$ of the base is less than about 14. For instance, the latent surfactant can be a carboxylic acid and the surfactant activator can be selected from the group consisting of Group I metal phosphates and amines.

DETAILED DESCRIPTION OF THE INVENTION

The compounds that are useful as free radical control agents in the practice of this invention are of the general structural formula: $(Z)\text{-}(R^1)_n$, wherein n represents an integer from 1 to about 6; wherein Z represents an aromatic or aliphatic moiety containing from 1 to about 20 carbon atoms; wherein $R^1$ represents a moiety of the structural formula:

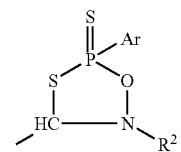

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

The free radical control agent can be of the structural formula:

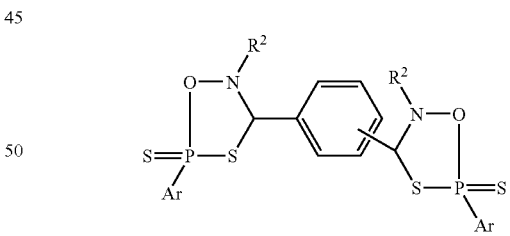

wherein $R^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms. Typically Ar will represents a p-methoxyphenyl group and $R^2$ will represent an alkyl group containing from 1 to about 8 carbon atoms. It is normally preferred for $R^2$ represents an isopropyl group. For instance, the free radical control agent can be of the structural formula:

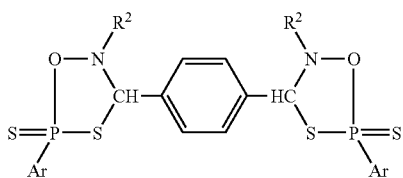

wherein R² represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms. Typically Ar will represents a p-methoxyphenyl group and R² will represent an alkyl group containing from 1 to about 8 carbon atoms. It is normally preferred for R² represents an isopropyl group.

The free radical control agent can also be of the structural formula:

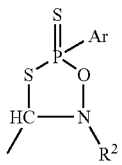

wherein wherein R² and R³ can be the same or different and are selected from moieties selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

The control agents of this invention can be readily prepared in a one step reaction at or close to ambient conditions by a [2+3]cycloaddition reaction between Lawesson's reagent (2,4-bis(4-methoxyphenyl)-1,3,2,4-dithiadiphosphetane 2,4-disulfide) and two equivalents of nitrone. A more detailed description of this reaction can be found in G Bertrand et al., J. Org. Chem., 60, 3904 (1995), the teachings of which are incorporated herein in their entirety with respect to the synthesis of the control agent.

The polymerization conditions that can be used include temperatures for polymerization typically in the range of from about 20° C. to about 110° C., more preferably in the range of from about 40° C. to about 90° C. and even more preferably in the range of from about 50° C. to about 80° C. The atmosphere may be controlled, with an inert atmosphere being preferred, such as nitrogen or argon. The molecular weight of the polymer is controlled via adjusting the ratio of monomer to control agent. Generally, the molar ratio of monomer to control agent is in the range of from about 5 to about 5000, more preferably in the range of from about 10 to about 2000, and most preferably from 10 to about 1500.

A free radical source is provided in the polymerization mixture, which can stem from spontaneous free radical generation upon heating or preferably from a free radical initiator. In the latter case the initiator is added to the polymerization mixture at a concentration high enough to for an acceptable polymerization rate (e.g., commercially significant conversion in a certain period of time). Conversely, a too high free radical initiator to control agent ratio will favor unwanted dead polymer formation through radical-radical coupling reaction leading to polymer materials with uncontrolled characteristics. The molar ratio of free radical initiator to control agent for polymerization are typically in the range of from about 3:1 to about 0.02:1.

Polymerization conditions also include the time for reaction, which may be from about 0.5 hours to about 72 hours, preferably in the range of from about 1 hour to about 36 hours, and more preferably in the range of from about 2 hours to about 18 hours. Conversion of monomer to polymer is preferably at least about 50%, more preferably at least about 80% and most preferably at least about 90%.

The polymerization process generally proceeds in a "living" type manner. Thus, generally an approximately linear relationship between conversion and number average molecular weight can be observed, although this is not a pre-requisite. The living character manifests itself by the ability to prepare block copolymers: hence, a polymer chain is first grown with monomer A, and then, when monomer A is depleted, monomer B is added to extend the first block of polymer A with a second block of polymer B. Thus, in some instances, particularly when the chain transfer constant of the control agent, Ct, is low (Ct being defined as the ratio of the transfer rate coefficient to the propagation rate constant), e.g., Ct less than 2, the molecular weight to conversion plot might not exhibit a linear trend. However, such a conversion plot does not necessarily indicate that block copolymer formation did not occur. Block copolymer formation through a living process can be demonstrated using analytical techniques such as polymer fractionation with selective solvent (of polymer A, polymer B, respectively), gradient elution chromatography and/or 2-dimensional chromatography. Block copolymers tend to microphase-separate and organize in a variety of morphologies that can be probed by physical techniques such as X-ray diffraction, dynamic mechanical testing, and the like.

Initiators, as discussed above, may be optional. When present, initiators useful in the polymerization mixture and the inventive process are known in the art, and may be selected from the group consisting of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, and azo compounds. Specific initiators include benzoylperoxide (BPO) and AIBN. The polymerization mixture may use a reaction media is typically either an organic solvent or bulk monomer or neat. Optionally, after the polymerization is over (e.g., completed or terminated) the thio-moiety (e.g., a dithio-moiety) of the control agent can be cleaved by chemical or thermal ways, if one wants to reduce the sulfur content of the polymer and prevent any problems associated with presence of the control agents chain ends, such as odor or discoloration. Typical chemical treatment includes the catalytic or stoichiometric addition of base such as a primary amine, acid or anhydride, oxidizing agents, such as hypochlorite salts, or reducing agents, such as Raney nickel.

The monomers that can be polymerized using the control agents and polymerization technique of this invention (and from which M, below, may be derived) include conjugated diolefin monomers and vinyl aromatic monomers. Some representative examples of monomers that can be polymerized utilizing the control agents of this invention include styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, 1,3-butadiene, ethylene, propylene, vinyl acetate, and combinations thereof. Functionalized versions of these monomers can also be used. Specific monomers or comonomers that can be used in the practice of this invention include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 4-acryloylmorpholine, vinyl benzoic acid (all isomers), diethylaminostyrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, 1,3-butadiene, isoprene, chloroprene, ethylene, vinyl acetate and combinations thereof.

In some embodiments of the polymers of this invention, a combination of hydrophobic and hydrophilic monomers may be used, either randomly or in separate blocks of a copolymer (e.g., thermoplastic elastomers, grafts, etc). The hydrophobic/hydrophilic nature of monomers may be determined according to the log P of the particular monomers, which is sometimes referred to as the octanol-water partition coefficient. Log P values are well known and are determined according to a standard test that determines the concentration of monomer in a water/1-octanol separated mixture.

Suitable hydrophilic monomers include, but are not limited to, acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Preferred hydrophilic monomers include acrylic acid, N,N-dimethyl acrylamide, dimethylaminoethyl methacrylate, quaternized dimethyl aminoethyl methacrylate, vinyl pyrrolidone, salts of acids and amines listed above, and combinations thereof.

Suitable hydrophobic monomers may be listed above and include, but are not limited to, acrylic or methacrylic acid esters of $C_1$-$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octa decanol, and the like, the alcohols having from about 1 to about 18 carbon atoms, preferably from about 1 to about 12 carbon atoms; styrene; polystyrene macromer, vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred hydrophobic monomers include n-butyl methacrylate, isobutyl methacrylate, t-butyl acrylate, t-butyl methacrylate, 2-ethylhexyl methacrylate, methyl methacrylate, vinyl acetate, vinyl acetamide, vinyl formamide, and mixtures thereof, more preferably t-butyl acrylate, t-butyl methacrylate, or combinations thereof.

In addition, monomers that polymerize in a ring closing method may also be used in this invention, including monomers that are of the formula: $CH_2=CH-X'-CH=CH_2$ where X' comprises from 1 to 20 non-hydrogen atoms. Such monomers are well known in the art. A specific example is $\{CH_2=CH-N(CH_3)_2-CH=CH_2\}^+\{Cl\}^-$.

In the broadest sense, an emulsion polymerization is any heterogeneous polymerization in an aqueous environment. Typically, these systems produce particles of polymer as product. Those skilled in the art recognize many variants of these heterogeneous polymerizations, including true emulsions, micro emulsions, mini emulsions, suspensions and dispersions. These processes are generally distinguished by differences in process, components or results, with specific factors including the presence, amount and type of surfactant required; presence, amount and type of initiator; presence, type and amount of monomer, including monomer solubility; polymerization kinetics; temperature; order of addition of the components, including the timing of addition of the components (e.g., monomer); solubility of the polymeric product; agitation; presence of co-solvents; resulting particle size; particle stability in the polymerization system toward coagulation or sedimentation; and other factors known to those skilled in the art. In some embodiments of this invention, systems that employ a shearing force or step to create small particle sizes are excluded.

One specifically preferred embodiment of the invention is a controlled heterogeneous polymerization reaction in an emulsion characterized by particle sizes ranging from 20 to 1000 nm, and preferably from 30 to 600 nm or from 40 to 300 nm. Polymerizations of this embodiment may have process parameters similar to those discussed above for "traditional" or "true" emulsion polymerizations. These emulsions are stable (on the order of many months with no observed coagulation or sedimentation), yet are prepared using surfactant in amounts less than 3% by weight to monomer.

The use of control agents under emulsion conditions offers other benefits associated with living kinetics (e.g., linear increase in molecular weight as a function of conversion). The controlled free radical emulsion polymerizations of the invention provide a high degree of control over molecular weight often with narrow molecular weight distribution (polydispersity ($M_w/M_n$) generally less than 2 and preferably between 1.1 and 1.8).

In the heterogeneous polymerization process of this invention, the control agent is combined with water, optionally surfactant, initiator, and at least one monomer. Polymerization conditions include a temperature in the range of from about 25° C. to about 150° C., preferably between about 35° C. and about 110° C., more preferably between about 40° C. and about 100° C., and most preferably between about 50° C. and about 90° C.

Polymerization is typically conducted at a pressure between about ambient pressure up to about 100 atmospheres. Polymerization conditions also include the time for reaction, which may be from about 0.5 hours to about 72 hours, preferably in the range of from about 1 hour to about 36 hours, more preferably in the range of from about 2 hours to about 18 hours.

Surfactants can be useful in polymerizations which are conducted with the control agents of this invention. Suitable surfactants include any species or mixture of species capable of stabilizing colloidal emulsions. Generally surfactants are amphiphilic molecules comprising both hydrophobic and hydrophilic regions, which are capable of adsorbing to surfaces. Surfactants may be small molecules or polymers, micelle forming or non-micelle forming and may be anionic, cationic, zwitterionic or nonionic. In some embodiments, it may be desirable to use mixtures of surfactants, for example to enhance particle stability or control particle formation. Surfactants can play an important role in determining particle size, particle distribution, particle formation and the stability of the resulting polymer emulsion, which are factors that those of skill in the art typically consider when choosing a surfactant for any specific embodiment. Typical amounts of surfactants range from about 0.01 to about 200% by weight relative to the monomer, with a more preferred range being from about 0.1 to about 5% by weight and more specifically preferred being from about 0.5 to about 3% by weight.

Suitable surfactants include anionic, small molecule surfactants including substituted or unsubstituted hydrocarbyl sulfates, sulfonates, carboxylates, phosphonates and phosphates, having between 6 and 30 carbon atoms per anionic functional group. When the hydrocarbyl group is substituted, it may have one or more hydrogen or carbon atoms replaced with another atom selected from the group consisting of nitrogen, sulfur, oxygen, silicon, fluorine, chlorine, bromine, and iodine. The hydrocarbyl may also have one or more hydrogen or carbon atoms replaced with a functionality such as a keto, ester, amide, ether, thioether and the like. Specific examples of anionic, non-polymeric surfactants include sodium dodecyl sulfate, sodium dodecylbenzene sulfonate, $C_{14}$-$C_{16}$ α-olefin sulfonate, oleoyl methyltaurine, alkyl sulfosuccinate, sodium stearate, alkyl substituted disulfonated diphenyloxide and nonylphenoxy oligo(ethylene glycol) sulfate. Ionic polymers can be used, including polyethyleneimine, polyacrylic acid, carboxymethyl cellulose and the like. Suitable cationic surfactants include cetyltrimethyl ammonium bromide, N-methyl(4-dodecylpyridinium bromide). Suitable nonionic surfactants include ethoxylated mono-, di- and trialkylphenols (degree of ethoxylation: 3 to 100, alkyl radical: $C_4$ to $C_{12}$), ethoxylated fatty alcohols (degree of ethoxylation: 3 to 100, preferably 6 to 50, alkyl radical: $C_6$ to $C_{20}$) and alkali metal and ammonium salts of alkylsulfates (alkyl radical: $C_8$ to $C_{18}$), of sulfuric half-esters of ethoxylated alkanols (degree of ethoxylation: 1 to 70, in particular 2 to 10, alkyl radical: $C_{10}$ to $C_{18}$) and of ethoxylated alkylphenols (degree of ethoxylation: 3 to 100, preferably 6 to 50, alkyl radical: $C_4$ to $C_{18}$) and alkali metal and ammonium salts of alkanesulfonic acids (alkyl radical: $C_{10}$ to $C_{18}$) and of alkylarylsulfonic acids (alkyl radical: $C_9$ to $C_{18}$). Further suitable surfactants, such as sulfosuccinates, are described in Houben-Weyl, Methoden der organischen Chemie, Volume XIV/1, Makromolekulare Stoffe, Georg-Thieme Verlag, Stuttgart, 1961, pages 192 to 208. Alternative surfactants include functional monomers, polymerizable surfactants and water-soluble surface-active polymers, including block copolymers, such as polyethyleneoxide-b-polypropyleneoxid-e-b-polyethyleneoxide (Pluronic®). Specific examples include polyvinyl alcohols, cellulose derivatives or vinylpyrrolidone-containing copolymers. A detailed description of further suitable protective colloids is given in Houben-Weyl, Methoden der organischen Chemie, Volume XIV/1, Makromolekulare Stoffe, Georg-Thieme-Verlag, Stuttgart, 1961, pages 411 to 420. Currently commercially available surfactants that are useful in the practice of this invention are listed in Table 1 on pages 10-11 on United States Patent Publication 2004/0073042, which is incorporated herein by reference.

An important aspect of the present invention is in-situ emulsification, which is achieved by reacting a "latent surfactant" with a "surfactant activator" to produce the surfactant for controlled emulsion polymerization. As used herein, the term "latent surfactant" refers to a compound or mixture of compounds that: (i) is soluble in a monomer-containing solution that is not miscible with water; and (ii) is not independently capable of producing a stabilized colloidal microemulsion at conventional surfactant levels from simple gentle mixing of the compound or mixture of compounds with monomer-containing solution and water. The term "surfactant activator" is used herein to describe a compound or mixture of compounds that: (i) is soluble in water; and (ii) is not independently capable of producing a stabilized colloidal microemulsion at conventional surfactant levels from simple gentle mixing of the compound or mixture of compounds with monomer-containing solution and water. For the present invention, water can be a reactant for in-situ emulsification reactions, but water alone cannot be the surfactant activator. The use of an in-situ emulsification technique in a controlled polymerization process that can be used in accordance with this invention is described in U.S. patent application Ser. No. 10/721,718, filed on Nov. 25, 2003. The teachings of U.S. patent application Ser. No. 10/721,718 are incorporated herein by reference in their entirety.

The fundamental principles for in-situ microemulsification are described by Prokopov and Gritskova (*Russ. Chem. Rev* 2001, 70, 791), who review its use in conventional free-radical polymerization of styrene using alkali-metal soaps prepared in situ via neutralization of fatty acids. As explained by Prokopov and Gritskova, the preparation of a carboxylate soap at a styrene-water interface during emulsification can produce a fine microemulsion because interfacial tension is decreased significantly by an abundance of emulsifier produced at the interface. By varying the nature of the carboxylic acid and the metal counter-ion used in the surfactant synthesis at the interface, it was possible to control the degree of dispersion and stability of the emulsion, as well as the resulting polystyrene latex produced via conventional free radical polymerization. In the present invention, the principles of in-situ microemulsification are expanded broadly to produce emulsions suitable for controlled polymerization via a wide range of methods utilizing conventional soap levels without added hydrophobes or specialized emulsification equipment.

In some embodiments, the surfactant for controlled polymerization may be produced by an acid/base neutralization reaction at the monomer/water interface. For some types of anionic surfactants, this may be accomplished, for example, via reaction of a monomer-soluble acid with an aqueous base, where the monomer-soluble acid is the latent surfactant and the base is the surfactant activator for in-situ emulsification. Suitable monomer-soluble acids include, for example, palmitic acid, oleic acid, dodecylbenzene sulfonic acid, lauryl sulfate, hexadecylsulfonic acid, dihexadecylphosphonic acid, hexadecylsuccinate half ester, and the monohexadecylamide of succinic acid. Suitable bases include, for example, hydroxides, carbonates and bicarbonates of alkali metal ions and quaternary ammonium ions, substituted and unsubstituted amines, and basic nitrogen-containing heterocycles. It will be evident to those skilled in the art that any aqueous base with a $pK_b$ less than about the $pK_a$ of the monomer-soluble acid also may be suitable. It also will be evident that hydroxides generated in situ via hydrolysis of moisture-sensitive compounds, such as sodium methoxide, sodium amide, potassium hydride and the like, also may be suitable as surfactant activators.

For some types of cationic surfactants, in situ synthesis during emulsification may be accomplished, for example, via reaction of a monomer-soluble base with an aqueous acid, where the monomer-soluble base is the latent surfactant and the acid is the surfactant activator. Suitable monomer-soluble bases include, for example, hexadecyldimethylamine, hexadecyldimethylamine oxide, and amphiphilic nitrogen-containing heterocycles. Suitable acids include for example mineral acids, sulfonic acids and phosphonic acids. It will be evident to those skilled in the art that any aqueous acid with a $pK_a$ less than about the $pK_b$ of the monomer-soluble base also may be suitable. It also will be evident that acids generated in situ via: hydrolysis of moisture-sensitive compounds, such as Lewis acids, acyl halides, acyl anhydrides, mineral acid anhydrides, hydrolyzable transition-metal halides, main group halides and the like, also may be suitable as surfactant activators.

In some embodiments, surfactant may be produced in situ by chemical reactions that attach hydrophilic functionality to a functionalized hydrophobe. For these embodiments, the functionalized hydrophobe is the latent surfactant and the reagent or reagents necessary for attaching the hydrophilic functionality serve as surfactant activator. For some types of surfactants this may be accomplished, for example, via reaction of a monomer-soluble electrophile with an aqueous nucleophile. Suitable electrophiles include for example: (i) hydrocarboyl halides; (ii) hydrocarboyl esters; (iii) hydrocarboyl anhydrides; (iv) hydrocarbyl isocyanates; (v) hydrocarbyl halides; and (vi) hydrocarbyl esters of sulfonic acids. Suitable surfactant activators include for example: (i) amine-functionalized hydrocarbylsulfates, hydrocarbylcarboxylates, hydrocarbylphosphates, hydrocarbylammonium salts; (ii) diethanol amine; (iii) diethylenetriamine and other aminoamines; (iv) amino-polyethyleneglycols and polyethyleneglycol ethers; (v) aminoglycosides; (vi) aminobetaines; (vii) hydroxides of alkali metal ions and quaternary ammonium ions; and (viii) hydrocarbylamines.

For some types of surfactants, in-situ synthesis and emulsification may be accomplished by reaction of a monomer-soluble nucleophile with an aqueous electrophile. Suitable nucleophiles include for example, hexadecylamine and hexadecyldimethylamine. Suitable electrophiles include for example succinic anhydride, dimethylsulfate and 1,3-propanesultone.

Many other reactions can be used to synthesize surfactants in situ, and the specific embodiments illustrated above are not intended to preclude any combination of latent surfactant/surfactant activator that produces a surfactant during emulsification. It will be evident to those skilled in the art that other latent surfactant/surfactant activator combinations may be suitable when the chemistries of surfactant synthesis and controlled polymerization are compatible.

The process of the invention does not necessarily require surfactant. For example, surfactant-free recipes can be used where the sulfate groups on a persulfate initiator impart the latex stability. In this case, relatively large ratios of initiator to monomer are used (e.g., 50:1 to 250:1) and large particles result (e.g., 300-600 nm). The ratios of components (e.g., initiators, surfactants, monomers, and control agents) in the polymerization mixture may be important and can vary widely depending on the particular application. The ratio of monomer to control agent can be used to determine the molecular weight of polymers produced using the controlled heterogeneous free radical polymerization processes of the invention. According to these processes, the number average molecular weight of the resulting polymers depends linearly on the number of control agents in the polymerization and the mass of monomer.

In some embodiments, the monomer to initiator ratio may be in the range of from about 10:1 to about 10,000:1, more preferably the range of from about 50:1 to about 10,000:1 and most preferably the range of from about 100:1 to about 5000:1. Another ratio that may be controlled is the ratio of equivalents of initiator to control agent, (with the assumption that the amount of initiator is approximately equivalent to the number of radical produced), which is typically in the range of from about 1:0.1 to about 1:10, more preferably the range of from about 1:0.3 to about 1:5 and most preferably the range of from about 1:0.4 to about 1:2. When a redox system is used, it may be present the ratio of initiator to reductant typically in the range of from about 1:0.1 to about 1:4, more preferably the range of from about 1:0.3 to about 1:2 and most preferably the range of from about 1:0.4 to about 1:1.6. The surfactant to monomer ratio may be controlled and is typically in the range of from about 0.0001 to about 2:1, more preferably the range of from about 0.001:1 to about 0.05:1 and most preferably the range of from about 0.001:1 to about 0.02:1 (although for some emulsions there may be no surfactant added at all where other reaction components perform that function). The percent solids may be in the range of from 0.001% to about 90% by volume. In some preferred applications, the novel aqueous polymer emulsions are produced with a solids content of at least about 40%, advantageously at least about 50%, by volume, based on the total aqueous polymer emulsion. The useful solids content for other applications is from 0.5 to 75% by volume. The preparation of the novel aqueous polymer emulsions is carried out according to the product by process definition of the subject according to the invention, as stated at the outset, i.e., by the free radical aqueous emulsion polymerization method in the presence of surface active materials and free radical polymerization initiators. The ratio of the aqueous phase to the total amount of the monomers used in both stages is chosen according to the desired solids content of the aqueous polymer emulsion to be prepared.

The emulsion process can be implemented in a batch, semi-batch or continuous mode. In one embodiment the reaction is operated in such a way as to convert the control agent into dormant chains early in the process. For example, the consumption of the control agent is substantially completed when the cumulative monomer conversion (defined as the ratio monomer converted at time t to the total monomer present in the recipe) is less than about 30%, more specifically less than about 20% and even more specifically less than about 10%. This can be performed by adjusting polymerization process variables, such as the sequence and feed-rate of addition of monomers, control agents, initiators, etc. For example, in a semi-batch polymerization process where a fraction of the monomer is introduced initially in the reactor and the remaining fraction fed over a period of time, the control agent is preferentially added in totality in the initial charge. In a continuous polymerization process (e.g., using either a recirculation loop or a series of continuously stirred tank reactors), the control agent is preferably fed in the upstream part of the continuous process. A preferred polymerization process is semi-batch, with the totality of the control agent fed to the initial charge and where the feed rate of the monomer stream is adjusted to a "starved feed regime", i.e., where the monomer to polymer ratio is maintained below 0.2, preferably 0.05, until the control agent is totally consumed (as measured by gas or liquid chromatography). Process variables that may coincide to control the monomer to polymer ratio are rate of monomer additions, initiator to monomer ratios, temperature and particle size.

A free radical source is provided in the polymerization mixture, which can stem from spontaneous free radical generation upon heating or preferably from a free radical initiator. In the latter case the initiator is added to the polymerization mixture at a concentration high enough to for an acceptable polymerization rate (e.g., commercially significant conversion in a certain period of time, such as listed below). Conversely, a too high free radical initiator to control agent ratio will favor unwanted dead polymer formation through radical-radical coupling reaction leading to polymer materials with uncontrolled characteristics. The molar ratio of free radical initiator to control agent for polymerization are typically in the range of from about 2:1 to about 0.02:1. The polymers formed with the chain transfer agents of this invention are believed to be grown via a degenerative transfer mechanism.

Block copolymers can easily be made utilizing the control agents of this invention by a two step or multiple step process. As used herein, "block copolymer"refers to a polymer comprising at least two segments of differing composition; having any one of a number of different architectures, where the monomers are not incorporated into the polymer architecture in a solely statistical or uncontrolled manner. Although there may be three, four or more monomers in single block-type polymer architecture, it will still be referred to herein as a block copolymer. In some embodiments, the block copolymer will have an A-B architecture (with "A" and "B" representing the monomers). Other architectures included within the definition of block copolymer include A-B-A, A-B-A-B, A-B-C, A-B-C-A, A-B-C-A-B, A-B-C-B, A-B-A-C (with "C" representing a third monomer), and other combinations that will be obvious to those of skill in the art. Block copolymers can be prepared a number of ways, including sequential addition of monomers or using multi-functional control agents described above. Of course with multi-functional control agents, the control agent may form a linking group between one or more blocks of the copolymers.

The block copolymers that can be synthesized with the control agents of this invention include one or more blocks of random copolymer together with one or more blocks of single monomers. Thus, a polymer architecture of A-R, A-R-B, A-B-R, A-R-B-R-C, etc. is included herein, where R is a random block of monomers A and B or of monomers B and C. Moreover, the random block can vary in composition or size with respect to the overall block copolymer. In some embodiments, for example, the random block R will account for between 5 and 80% by weight of the mass of the block copolymer. In other embodiments, the random block R will account for more or less of the mass of the block copolymer, depending on the application. Furthermore, the random block may have a compositional gradient of one monomer to the other (e.g., A:B) that varies across the random block in an algorithmic fashion, with such algorithm being either linear having a desired slope, exponential having a desired exponent (such as a number from 0.1-5) or logarithmic. The random block may be subject to the same kinetic effects, such as composition drift, that would be present in any other radical copolymerization and its composition, and size may be affected by such kinetics, such as Markov kinetics. Any of the monomers listed elsewhere in this specification may be used in the block copolymers of this invention.

A "block" within the scope of the block copolymers of this invention typically comprises about 10 or more monomers of a single type (with the random blocks being defined by composition and/or weight percent, as described above). In preferred embodiments, the number of monomers within a single block is about 15 or more, about 20 or more or about 50 or more. However, in an alternative embodiment, the block copolymers of this invention include blocks where a block is defined as two or more monomers that are not represented elsewhere in the copolymer. This definition is intended to encompass adding small amounts of a second monomer at one or both ends of a substantially homopolymeric polymer. In this alternative embodiment, the same copolymer architectures discussed above apply. This definition is therefore intended to include telechelic polymers, which include one or more functional end groups capable of reacting with other molecules. Thus, generally, a telechelic polymer is a block copolymer with in the definitions of this invention. The functional groups present at one or both ends of a telechelic polymer may be those known to those of skill in the art, including, for example, hydroxide, aldehyde, carboxylic acid or carboxylate, halogen, amine and the like, which have the ability to associate or form bonds with another molecule. Likewise, the block copolymers of the invention are intended to encompass telechelic polymers containing bifunctional groups, such as allyl-terminated or vinyl-terminated telechelics, sometimes referred to as macromonomers or macromers because of their ability to participate in polymerization reactions through the terminal functional group.

Combining the above embodiments provides a particularly powerful method of designing block copolymers. For example, a block copolymer may have the architecture F-A-B-F, where F represents functional groups that may be the same or different within a single F-A-B-F structure (which, therefore, may encompass F-A-B-F). Other block copolymer architectures within the scope of this invention include A-R-B-F and F-A-R-B-F. Other architectures will be apparent to those of skill in the art upon review of this specification. Indeed, without wishing to be bound by any particular theory, it is the living nature of the emulsions of this invention that provide the ability to even make these novel block copolymers.

In one embodiment, block copolymers are assembled by the sequential addition of different monomers or monomer mixtures to living polymerization reactions. In another embodiment, the addition of a pre-assembled functionalized block (such as a telechelic oligomer or polymer) to a living free radical polymerization mixture yields a block copolymer. Ideally, the growth of each block occurs to high conversion. Conversions are determined by size exclusion chromatography (SEC) via integration of polymer to monomer peak. For UV detection, the polymer response factor must be determined for each polymer/monomer polymerization mixture. Typical conversions can be 50% to 100% for each block. Intermediate conversion can lead to block copolymers with a random copolymer block separating the two or more homopolymer blocks, depending on the relative rates of polymerization and monomer addition. At high conversion, the size of this random block is sufficiently small such that it is less to affect polymer properties such as phase separation, thermal behavior and mechanical modulus. This fact can be intentionally exploited to improve polymerization times for many applications without measurably affecting the performance characteristics of the resulting polymer. This is achieved by intentionally "killing" or terminating the living nature of the polymerization when a desired level of conversion (e.g., >80%) is reached by neutralizing the control agent, for example by introducing acids, bases, oxidizing agents, reducing agents, radical sources, scavengers, etc. In the absence of control agent, the polymerization continues uncontrolled (typically at much higher reaction rates) until the remaining monomer is consumed. Block copolymer can also be created by grafting monomers, monomer mixtures, oligomers or polymers having multiple available functional groups.

In other embodiments, block copolymers can be prepared by grafting processes, preparation of telechelic polymers, preparation of macromonomers, etc. In these embodiments, at least one polymer segment is derived from a living or controlled process of the invention, while other segments can be derived from any polymerization process, including, for example, controlled or uncontrolled radical polymerization, condensation polymerization, Ziegler-Natta and related processes, Ring-Opening Metathesis Polymerization, ionic polymerization, surface modification or grafting, or other addition or step growth processes.

Block copolymers allow the combination of potentially diverse polymer properties (such as hard/soft and/or hydrophilic/hydrophobic (amphiphilic) blocks) into a single polymer chain. Hard/soft block copolymers combine segments with significantly different glass transition temperatures (Tg). A typical hard/soft copolymer pairs a relatively "hard" block (e.g., styrene) with a relatively "soft" block (e.g., butyl acrylate). The resulting materials can possess performance attributes not found in any of the constituent segments. The presence of microphase separation and various phase morphologies in block copolymers is associated with unique performance attributes of many block copolymers. For example, by combining the stiffness or rigidity characteristic of hard materials with the compliance of soft materials, block copolymers may exhibit advantageous properties, such as processability under melt conditions, elasticity, resistance to abrasion and cracking and desired creep characteristics (corresponding to the material's ability to hold its shape under external stresses) depending on morphology, making them appropriate for use as extrudable bulk materials, coatings and separation media. The exact properties of a hard/soft copolymer depend significantly on the difference between the glass transition temperatures of the constituent blocks; accordingly, selection of monomers having glass transition temperatures a particular distance apart can lead to hard/soft block copolymers having particular desired characteristics. Thus, while for one application it may be appropriate to combine blocks having glass transition temperatures that differ by, for example, 20° C., the choice of Tg (and therefore of materials) depends on the application. Likewise, the amphiphilic block copolymers produced according to the invention display combinations of hydrophobic and hydrophilic properties that make such materials appropriate for use as surfactants or dispersants, scavengers, surface treatments and the like. Different block sizes over all ratios of monomers and molecular weights lead to families of novel compounds, for example thermoplastics, elastomers, adhesives, and polymeric micelles.

Multi-arm or star polymers can be generated using initiators capable of initiating multiple free radical polymerizations under the controlled conditions of the invention. Such initiators include, for example polyfunctional chain transfer agents, discussed above. Following initiation, the growth of each arm is controlled by the same living kinetics described for linear polymers, making it possible to assemble star polymers whose arms include individual homopolymers as well as di, tri or higher order block copolymers. Alternatively, multi-arm polymers are formed by growing end-functionalized oligomers or polymers followed by the addition of a cross-linking monomer such as ethylene glycol diacrylate, divinyl benzene, methylene bisacrylamide, trimethylol propane triacrylate, etc. The small hydrodynamic volume of star polymers produced according to these methods provides properties such as low viscosity, high $M_w$, and high functionality useful in applications such as rheology control, thermosets, and separation media. Similarly, the inclusion of branched or multiple ethylenically unsaturated monomers enables the preparation of graft polymers, again exhibiting the living kinetics characteristic of this invention. The existence of a block copolymer according to this invention is determined by methods known to those of skill in the art, including nuclear magnetic resonance (NMR), measured increase of molecular weight upon addition of a second monomer to chain-extend a living polymerization of a first monomer, microphase separation (e.g., long range order, microscopy and/or birefringence measurements), mechanical property measurements, (e.g., elasticity of hard/soft block copolymers), thermal analysis and chromatography (e.g., absence of homopolymer).

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this experiment the bis-oxathiazapholine adduct of α,α'-bisisopropyl-N,N'-(1,4-phenylene)nitrone (BIN) was synthesized utilizing a reaction that can be depicted as follows:

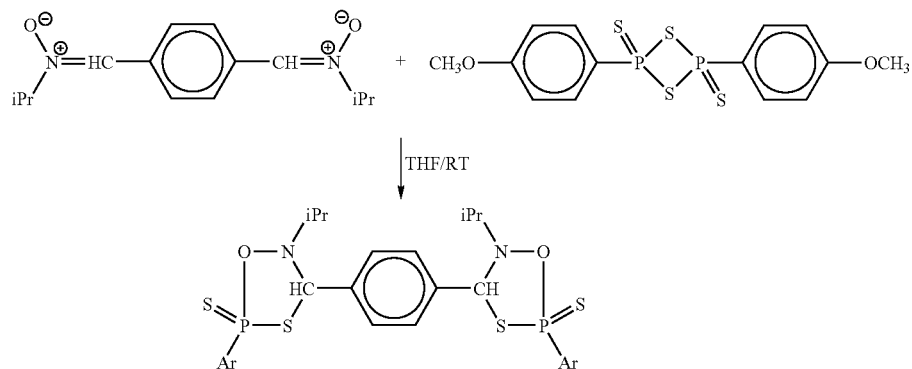

In the procedure utilized a 250 ml Erlenmeyer flask containing a magnetic stir bar was charged with 4.96 grams (~0.02 moles) of α,α'-bisisopropyl-N,N'-(1,4-phenylene)nitrone, 50 ml of tetrahydrofuran (THF), and 8.08 grams (~0.02 moles) of Lawesson's reagent (2,4-Bis(4-methoxy phenyl)-1,3-dithia 2,4-diphosphetane-2,4-disulfide). Lawesson's reagent has the chemical structural formula:

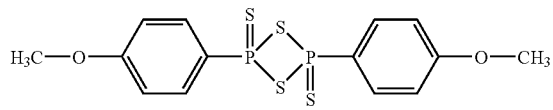

and is in the form of a pale yellow crystalline powder having a melting point of 221° C.-230° C. (430° F.-446° F.).

Upon stirring, the mixture rapidly became a clear yellow solution. After stirring overnight, some product had precipitated from solution. Then, 200 ml of water was slowly added to the stirred mixture to completely precipitate a fresh-colored solid. Product was filtered off and air dried to give 9.5 grams of crude product (~73% yield). P-31 NMR indicated that the material was about 98% pure with a sharp P-31 chemical shift of +18.2 ppm (relative to phosphoric acid at 0 ppm).

EXAMPLE 2

In this experiment a controlled emulsion polymerization of styrene monomer was conducted utilizing the bis-oxathiazaphospholine adduct synthesized in Example 1 as the free radical control agent. In the procedure used a three-necked round bottomed flask having a capacity of 500 ml was charged with 1.84 grams (about 0.00282 moles) of the bis-oxathiazaphospholine adduct, 10.0 grams of methylene chloride, 6.0 grams of oleic acid, and 100 grams of styrene. A mechanical paddle stirrer, condenser, nitrogen inlet and pot thermometer were attached to the flask. Then, the system was flushed with a slow nitrogen purge while warming under vigorous stirring to a temperature of about 55° C. (131° F.). At that point, the solution appeared to be uniform.

An aqueous emulsifier solution was made by dissolving 4.0 grams of potassium persulfate, 4.0 grams of potassium triphosphate, and 1.9 grams of 85% potassium hydroxide (KOH) pellets in 250 ml of distilled water in a separate container. The aqueous emulsifier solution was added (all at once) to the stirred styrene solution. An emulsion quickly formed and it was rapidly heated to a temperature of about 75° C. (167° F.). After approximately 3 hours the emulsion appeared to invert but heating was continued for another 2 hours. The inverted emulsion was broken by the addition of dilute aqueous hydrochloric acid (HCl) solution, saturated sodium chloride brine, and toluene. The top organic layer was then decanted off and dried to give 67 grams of polymer (about 67% conversion). A small sample of this polymer was dissolved in methylene chloride and reprecipitated in isopropanol. This sample was submitted for P-31 NMR analysis to confirm the presence of phosphorous in the polymer derived from the oxathiazaphospholine control agent. Strong new phosphorous resonances at 86, 9.9, 9.6 and 9.1 ppm were observed indicating that none of the original bis-oxathiazaphospholine remained (18.2 ppm) and that new phosphorous-containing polymer functionality was formed. SEC analysis against known polystyrene standards showed that the polymer had a number average molecular weight ($M_n$) of 38,400 and polydispersity (PDI) of 1.2.

EXAMPLE 3

In this experiment styrene monomer was again polymerized with the bis-oxathiazaphophospholine adduct made in Example 1. In the procedure used a 250 ml three-neck round bottom flask equipped with a magnetic stir bar, was charged with 3.0 grams (about 0.0046 moles) of the bis-oxathiazaphospholine adduct, 100 grams (0.95 moles) of styrene, and 10.0 grams of mixed xylenes. A condenser, nitrogen inlet, and pot thermometer then attached to the flask. The mixture was heated to a temperature of 125° C. while being stirred under a slow nitrogen purge and was maintained at that temperature for 18 hours. The mixture became a viscous dark brown liquid. It was diluted with toluene and pour into a teflon-lined pan. The solvents were allowed to evaporate from the polystyrene in a hood overnight followed by being heated to a temperature of 70° C. (158° F.) in a circulating air oven for several hours. A crude yield of 100.5 grams was attained which represents a conversion of about 100 percent. SEC analysis of the crude resin showed that it had a number average molecular weight ($M_n$) of 35,000 and a polydispersity (PDI) of 1.78.

EXAMPLE 4

In this experiment a styrene/n-butyl acrylate block copolymer was made by controlled polymerization. In the procedure used a 250 ml three-neck round bottom flask equipped with a magnetic stir bar was charged with 20.0 grams of the oxathiazaphospholine resin synthesized in Example 3, 40.0 grams (0.312 moles) of n-butyl acrylate, and 20.0 grams of mixed xylenes. This mixture was stirred overnight at room temperature to obtain a uniform solution. Then, 0.2 grams of AIBN was added to the solution. A condenser, pot thermometer, and nitrogen inlet were attached to the flask and the solution was slowly heated to a temperature of about 60° C. (140° F.). The exotherm from the polymerization increased the temperature of the solution to about 135° C. (275° F.). After the exotherm subsided, the temperature was maintained at 75° C. (167° F.) for 2 hours. The reaction mixture was then poured into a teflon-lined pan in a hood and the solvent and excess monomer was allowed to evaporate overnight. The reaction product was further dried by maintaining the Teflon-lined pan in a circulating air oven at 70° C. (158° F.) until a constant weight of 48.1 grams was attained (about 80% conversion).

The polymer recovered was sticky, opaque, and off-white in color. A small portion of this polymer was dissolved in tetrahydrofuran (THF) and reprecipitated from isopropanol for analysis. SEC analysis versus polystyrene standards gave a single mono-modal peak indicating a number average molecular weight (Mn) of 29,500 with a polydispersity (PDI) of 2.09. To further confirm the composition of the copolymer, proton NMR was also conducted on the reprecipitated copolymer. The ratio of aromatic protons to —O—CH$_2$— protons from the ester indicate a composition of 20% styrene and 80% butyl acrylate. This information taken together indicates that block copolymer formation was accomplished.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which would be within the full-intended scope of the invention as defined by the following appended claims.

What is claimed is:

1. A process for producing a polymer by controlled polymerization which comprises polymerizing at least one monomer in the presence of a free radical control agent of the structural formula: (Z)-(R$^1$)$_n$, wherein n represents an integer from 1 to about 6; wherein Z represents an aromatic or aliphatic moiety containing from 1 to about 20 carbon atoms; wherein R$^1$ represents a moiety of the structural formula:

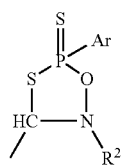

wherein R$^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

2. A process as specified in claim 1 wherein the free radical control agent is of the structural formula:

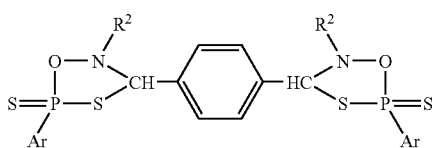

wherein R$^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

3. A process as specified in claim 2 wherein Ar represents a p-methoxyphenyl group.

4. A process as specified in claim 3 wherein R$^2$ represents an alkyl group containing from 1 to about 8 carbon atoms.

5. A process as specified in claim 3 wherein R$^2$ represents an isopropyl group.

6. A process as specified in claim 1 wherein the molar ratio of the monomers to control agent is in the range of from about 5 to about 5000.

7. A process as specified in claim 2 wherein the molar ratio of the monomers to control agent is in the range of from about 10 to about 2000.

8. A process as specified in claim 1 wherein the polymerization is initiated with a free radical initiator, and wherein the molar ratio of free radical initiator to the control agent is within the range of about 3:1 to about 0.02:1.

9. A process as specified in claim 1 wherein the polymerization is conducted at a temperature which is within the range of from about 20° C. to about 110° C.

10. A process as specified in claim 1 wherein the control agent is of the structural formula:

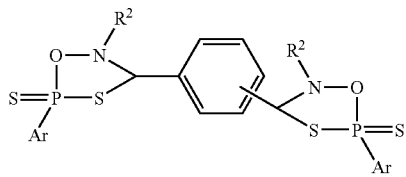

wherein R$^2$ represents a moiety selected from the group consisting of alkyl groups, alkenyl groups, alkynyl groups, aryl groups, heteroaryl groups, and alkaryl groups; wherein the alky groups, alkenyl groups, alkynyl groups, aryl groups, heteroaryl groups, and alkaryl groups can be substituted, unsubstituted, linear, branched or cyclic; and wherein Ar represents a p-alkoxyphenyl group having an alkoxy moiety that contains from 1 to 8 carbon atoms.

11. A process as specified in claim 10 wherein R$^2$ represents an alkyl group containing from 1 to about 8 carbon atoms.

12. A process as specified in claim 11 wherein Ar represents a p-methoxyphenyl group.

13. A process as specified in claim 11 wherein R$^2$ represents an isopropyl group.

14. A process as specified in claim 1 wherein the polymerization is conducted for a sufficient period of time to result in the production of a polymer, wherein the polymerization is initiated with a free radical initiator, and wherein the aqueous polymerization medium is substantially void of unreacted initiator.

15. A process as specified in claim 1 wherein the polymerization results in the production of polymer chains, and wherein at least about 80 percent of the polymer chains exhibit living polymerization kinetics.

16. A process as specified in claim 1 wherein the polymerization results is the production of a polymer having a polydispersity of less than about 2.0.

17. A process as specified in claim 1 wherein the molar ratio of the monomers to control agent is in the range of from about 10 to about 1500.

18. A process as specified in claim 1 wherein the polymerization is conducted at a temperature which is within the range of from about 40° C. to about 90° C.

19. A process as specified in claim 1 wherein the polymerization is conducted at a temperature which is within the range of from about 50° C. to about 80° C.

20. A process as specified in claim 1 wherein said monomer is styrene and wherein said polymer is polystyrene.

* * * * *